Figure 1:
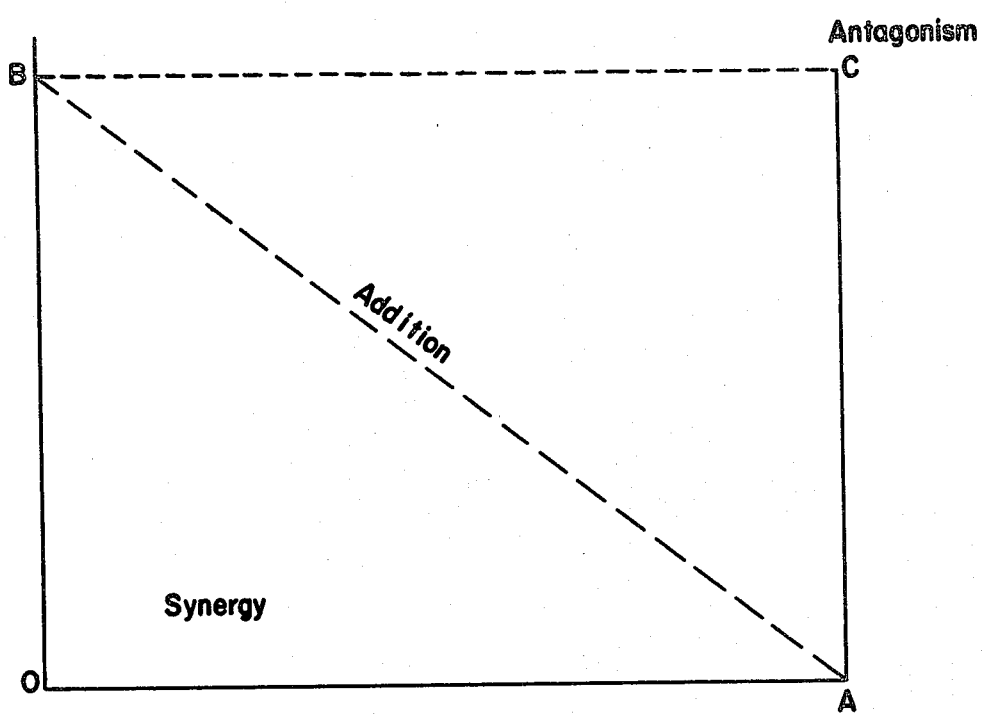

United States Patent [19]

Sykes

[11] 4,420,474
[45] Dec. 13, 1983

[54] SYNERGISTIC ANTIFUNGAL COMPOSITIONS

[75] Inventor: Richard B. Sykes, Rocky Hill, N.J.

[73] Assignee: E. R. Squibb & Sons, Inc., Princeton, N.J.

[21] Appl. No.: 85,161

[22] Filed: Oct. 15, 1979

[51] Int. Cl.³ .................... A61K 35/00; A61K 31/415
[52] U.S. Cl. .................................. 424/121; 424/120; 424/273 R
[58] Field of Search ........................... 424/121, 273 R

[56] References Cited

U.S. PATENT DOCUMENTS 3,076,746  2/1963  Arai ..................................... 424/121

OTHER PUBLICATIONS

Moody et al., 18th ICAAC Abstract 61 (1978).
Ansehn, Curr. Therap. Res., 22 pp. 92–99 (1977).
Chan et al., Asian J. of Med. 8 pp. 325–327 (1972).

*Primary Examiner*—Jerome D. Goldberg
*Attorney, Agent, or Firm*—Lawrence S. Levinson; Donald J. Barrack

[57] ABSTRACT

Synergistic activity against *Candida albicans* and *Trichomonas vaginalis* is obtained when an antifungal imidazole is combined with an antimicrobial agent selected from the group anisomycin, ascomycin, azalomycin F, brefeldin A, copiamycin, EM4940A, or EM4940B.

1 Claim, 1 Drawing Figure

SYNERGISTIC ANTIFUNGAL COMPOSITIONS

BACKGROUND OF THE INVENTION

Due to the widespread incidence of vaginitis, the topical antifungal market has increased significantly over the years. Until relatively recently the market has been dominated by the polyene antibiotics nystatin and amphotericin B. Now, certain imidazole derivatives have been found to have antifungal, antibacterial and antiprotozoal activity. Currently, miconazole, econazole and clotrimazole, three imidazole derivatives, are marketed as antifungal agents.

The currently marketed imidazole antifungal agents are active against *Candida albicans* when administered topically, orally and by intravenous infusion. Actual use of these compounds is limited, however, mostly to topical application. This limitation of utility is due to such practical considerations as adverse side effects and extensive metabolism.

While *Candida albicans* is thought to be the principal causative agent of vulvovaginitis, *Trichomonas vaginalis* has also been implicated as a causative agent, and unfortunately, the antifungal imidazoles do not have good activity against this organism.

DESCRIPTION OF THE INVENTION

Synergistic activity against *Candida albicans* and *Trichomonas vaginalis* is obtained when an antifungal imidazole is combined with an antimicrobial agent selected from the group anisomycin, ascomycin, azalomycin F, brefeldin A, copiamycin EM4940A or EM4940B.

With the exception of EM4940A and EM4940B, each of the non-imidazole components of the synergistic combination of this invention (and methods for their preparation) are disclosed in the literature.

Anisomycin (2-methoxybenzyl)-3,4-pyrrolidinediol,3-acetate) is an antiprotozoan agent discovered in the 1950's and described in U.S. Pat. No. 2,691,618, and in *J.A.C.S.*, 76, 4053 (1954). This compound shows activity against *Trichomonas vaginalis*, but not against *Candida albicans*.

Ascomycin is an antifungal agent described in U.S. Pat. No. 3,244,592, issued Apr. 5, 1966. The patent states that "ascomycin is clearly ineffective on Candida." No mention is made in in the patent of ascomycin's activity against Trichomonas.

Asalomycin F is a broad spectrum antimicrobial agent which is described in U.S. Pat. No. 3,076,746, issued Feb. 5, 1979. The patent sets forth biological test results showing the compound to be active against *Candida albicans* and *Trichomonas vaginalis*.

Brefeldin A, also known as ascotoxin, decumbin and cyanein, is an antifungal agent described in U.S. Pat. No. 3,896,002, issued July 22, 1975. As described in Helv. Chim. Acta, 46, 1235 (1963), brefeldin A is active against *Candida albicans*.

Copiamycin is an antifungal agent related to, but not identical with, azalomycin F (see *Appl. Microbiol.*, 21 (6): 986-89 (1971).Like azalomycin F, it exhibits activity against *Candida albicans* and *Trichomonas vaginalis*. Netherlands Pat. No. 6,511,353 published in 1966 describes the compound's preparation.

EM4940A and EM4940B (3,4-dihydro-4-hydroxy-5-(3-hydroxy-2-pyridinyl)-4-methyl-2H-pyrrole-2-carboxamide, the 2,4-trans and 2,4-cis isomers respectively) are disclosed in copending U.S. Pat. application Ser. No. 70,287 filed Aug. 27,1979, the disclosure of which is incorporated herein by reference. The compounds are said to be active against *Trichomonas vaginalis*.

The imidazole component of the synergistic mixture of this invention must have activity against *Candida albicans*.

While in its broadest aspects this invention encompasses the use of any antifungal imidazole meeting the above criteria as a component of its synergistic composition, certain classes of imidazoles are preferred.

One preferred group of imidazoles which can be used in this invention are the 1-($\beta$-aryl)-ethyl imidazole ethers and amines. As disclosed in U.S. Pat. No. 3,717,655, issued Feb. 20, 1973, antifungal and antibacterial activity is exhibited by imidazoles having the structural formula

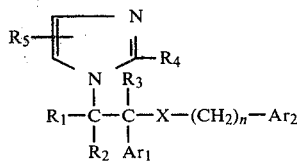

and therapeutically active salts thereof, wherein:

$R_1$, $R_2$ and $R_3$ each is hydrogen or alkyl of 1 to 6 carbons;

X is —O— or —NH—;

n is 0, 1 or 2;

$Ar_1$ is phenyl, substituted phenyl, thienyl or halothienyl, wherein said substituted phenyl has at least one halogen, alkyl of 1 to 6 carbons or alkoxy of 1 to 6 carbons, substituent;

$Ar_2$ is phenyl, substituted phenyl or $\alpha$-tetralyl, wherein said substituted phenyl has at least one halogen, alkyl of 1 to 6 carbons, alkoxy of 1 to 6 carbons, cyano, nitro or amino substituent;

$R_4$ is hydrogen, methyl or ethyl; and $R_5$ is hydrogen or methyl; provided that:

(i) when X is —NH—, $R_3$ is hydrogen;

(ii) when $Ar_2$ is substituted phenyl having at least one nitro or amino substituent, X is —O— and n is 0;

(iii) when $Ar_2$ is $\alpha$-tetralyl, X is —NH— and n is 0; and (iv) when X is —O— and $Ar_2$ is phenyl or substituted phenyl having at least one halogen, alkyl of 1 to 6 carbons, alkoxy of 1 to 6 carbons of cyano substituent, n is 1 or 2.

Miconazole (1-[2-(2,4-dichlorophenyl)-2-[(2,4-dichlorophenyl)methoxy]ethyl]-1H-imidazole) and econazole (1-[2-[(4-chlorophenyl)methoxy]-2-(2,4-dichlorophenyl)ethyl]-1H-imidazole), two commercial antifungal agents encompassed by formula I, are the preferred 1-($\beta$-aryl)ethyl imidazole ethers. The ethers of formula I are preferred over the amines.

A second preferred group of imidazoles are the imidazolylethoxy derivatives of pyrazolo-[3,4-b]pyridine-5-methanols. As disclosed in U.S. Pat. application Ser. No. 923,418, filed July 10, 1978 (the disclosure of which is incorporated herein by reference ) antifungal and antibacterial activity is exhibited by imidazoles having the structural formula

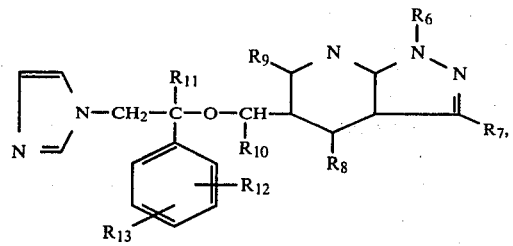

and physiologically acceptable acid addition salts thereof, wherein:

$R_6$ is hydrogen, alkyl of 1 to 7 carbons, phenyl, phenylalkyl wherein the alkyl group has 1 to 7 carbons, or cycloalkyl of 3 to 7 carbons;

$R_7$, $R_9$, $R_{10}$ and $R_{11}$ each is hydrogen, alkyl or phenyl;

$R_8$ is hydrogen, hydroxy, alkoxy of 1 to 7 carbons, alkylthio of 1 to 7 carbons, phenoxy, phenylalkoxy wherein the alkoxy group has 1 to 7 carbons, halogen or a basic nitrogen group

wherein $R_{14}$ and $R_{15}$ each is hydrogen, alkyl, phenyl or substituted phenyl wherein the phenyl substituent is halogen, hydroxy, alkoxy of 1 to 7 carbons, alkyl of 1 to 7 carbons, mercapto, aklylthio of 1 to 7 carbons, cyano or nitro; and $R_{12}$ and $R_{13}$ each is hydrogen, halogen, hydroxy, alkylthio of 1 to 7 carbons, alkyl of 1 to 7 carbons or nitro. Those compounds of formula II wherein $R_{12}$ and $R_{13}$ are ortho-chloro and para-chloro respectively are preferred. The preferred compound of formula II is 4-chloro-5-[[1-(2,4-dichlorophenyl)-2-(1H-imidazol-1-yl)-ethoxy]methyl]-1-ethyl-3-methyl-1H-pyrazolo[3,4-b]-pyridine, or salts thereof, and more specifically the monohydrochloride salt of that compound.

A third preferred group of imidazoles are the imidazolylethoxy derivatives of pyridin-5-methanols. As disclosed in U.S. Pat. application Ser. No. 954,730, filled Oct. 25, 1978 (the disclosure of which is incorporated herein by reference) antifungal and antibacterial activity is exhibited by imidazoles having the structural formula

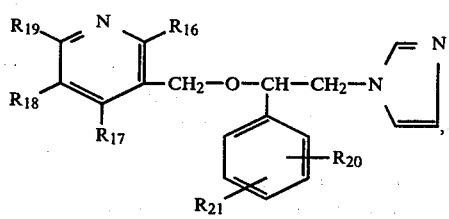

and physiologically acceptable acid-addition salts thereof, wherein: $R^{16}$, $R^{17}$, $R^{18}$, $R^{19}$, $R^{20}$, and $R^{21}$, each is hydrogen, hydroxy, halogen, alkoxy of 1 to 7 carbons, alkylthio of 1 to 7 carbons or alkyl of 1 to 7 carbons. The preferred compound of formula III is 2,4-dichloro-5-[[1-(2,4-dichlorophenyl)-2-(1H-imidazol-1-yl)ethoxy]methyl]-pyridine, or salts thereof, and more specifically, the monohydrochloride salt thereof.

A fourth preferred group of imidazoles which can be used in this invention are the N-trityl-imidazoles. As disclosed in U.S. Pat. Nos. 3,660,577, issued May 2, 1972 and 3,705,172, issued Dec. 5, 1972, antifungal activity is exhibited by imidazoles having the formula

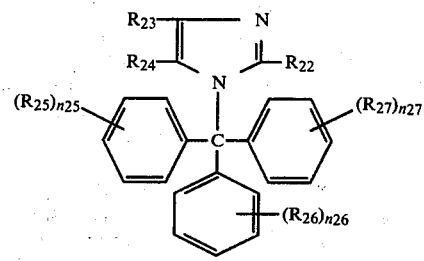

and pharmaceutically acceptable salts thereof, wherein:

$R_{22}$, $R_{23}$ and $R_{24}$ each is hydrogen, alkyl of 1 to 4 carbons or phenyl;

$R_{25}$, $R_{26}$ and $R_{27}$ each is alkyl of 1 to 12 carbons, halogen, nitro, trifluoromethyl, cyano, alkylthio of 1 to 4 carbons, or alkoxy of 1 to 4 carbons; and $n_{25}$, $n_{26}$ and $n_{27}$ each is 0, 1 or 2. Within the genus of compounds represented by formula IV, a preferred subgenus comprises those compounds of formula IV wherein $R_{22}$, $R_{23}$ and $R_{24}$ each is hydrogen. Another preferred subgenus comprises those compounds of formula IV wherein $R_{22}$, $R_{23}$, and $R_{24}$ each is hydrogen and $n_{25}$ and $n_{27}$ each is 0. The most preferred subgenus comprises those compounds of formula IV wherein $R_{22}$, $R_{23}$ and $R_{24}$ each is hydrogen, $n_{25}$ and $n_{27}$ each is 0, $n_{26}$ is 1 and $R_{26}$ is halogen, nitro, trifluoromethyl, cyano, methylthio, or methoxy. Clotrimazole (1-[(2-chlorophenyl)disphenylmethyl]-1H-imidazole) is the most preferred compound of formula IV.

A fifth preferred group of imidazoles which can be used in this invention are the substituted N-alkyl imidazoles. As dislosed in U.S. Pat. No. 4,078,071, issued Mar. 7, 1978, antifungal, antibacterial and antiprotozoal activity is exhibited by compounds having the formula

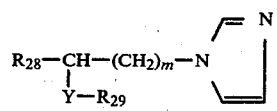

and pharmaceutically acceptable acid additon salts thereof, wherein:

$R_{28}$ and $R_{29}$ each is phenyl, phenylalkyl (wherein the alkyl portion of the molecule is a straight chain alkyl of 1 to 8 carbons), or phenylalkenyl (wherein the alkenyl portion of the molecule is a straight chain alkenyl of 2 to 8 carbons), or one of the above groups substituted in the phenyl ring with one or more alkyl of 1 to 4 carbons, halogen or trifluoromethyl groups;

Y is oxygen or sulfur; and m is an integer of 1 to 8; provided that when $R_{28}$ is phenyl or substituted phenyl, m is an integer of 2 to 8. The preferred compound of formula V is butoconazole (1-[2-[(2,6-dichlorophenyl)thio]-4-(4-chlorophenyl)-butyl]imidazole), or salts thereof, and more specifically the mononitrate salt.

A sixth preferred group of imidazoles which can be used in this invention are the 1-aryl-2-(1-imidazolyl)alkyl ethers and thioethers. As disclosed in U.S. Pat. No.

4,062,966, issued Dec. 13, 1977, antifungal activity is exhibited by compounds having the formula

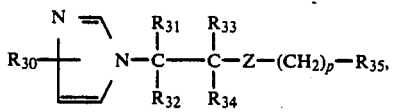   VI and pharmaceutically acceptable acid addition salts thereof, wherein;

$R_{30}$, $R_{31}$, $R_{32}$ and $R_{33}$ each is hydrogen or alkyl of 1 to 6 carbons;

$R_{34}$ is thienyl, halothienyl, phenyl or substituted phenyl, said substituents being halogen, alkyl of 1 to 6 carbons or alkoxy of 1 to 6 carbons;

Z is oxygen or sulfur;

p is 1 or 2; and $R_{35}$ is an aromatic heterocyclic group or substituted heterocyclic group, said substituents being halogen, alkyl of 1 to 6 carbons or alkoxy of 1 to 6 carbons.

Preferred subgeneric groups of imidazoles of formula VI include those compounds wherein $R_{34}$ is phenyl or substituted phenyl (2,4-dichlorophenyl is particularly preferred); $R_{30}$, $R_{31}$, $R_{32}$ and $R_{33}$ each is hydrogen; p is 1; and $R_{35}$ is thienyl or halothienyl. The preferred compound of formula VI is tioconazole (1-[2-[(chloro-3-thienyl)methoxy[-2-(2,4-dichlorophenyl)ethyl]-1H-imidazole).

A seventh preferred group of imidazoles which can be used in this invention are the 1-(1,3-dioxolan-2-ylmethyl)-1H-imidazoles. As disclosed in U.S. Pat. No. 4,144,346, issued Mar. 13, 1979, antifungal and antibacterial activity is exhibited by compounds having the formula

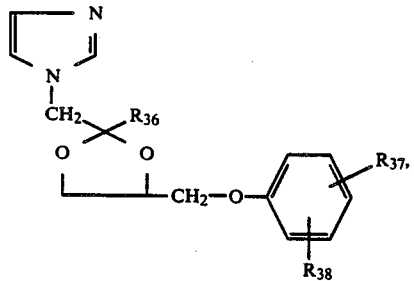   VII and the pharmaceutically acceptable acid addition salts thereof, wherein;

$R_{36}$ is phenyl or phenyl substituted with 1, 2 or 3 halo, alkyl (of 1 to 6 carbons) or alkoxy (of 1 to 6 carbons) groups;

$R_{37}$ is —N=C=S(isothiocyanato); amino, alkylamino or dialkylamino, wherein each alkyl group has 1 to 6 carbons;

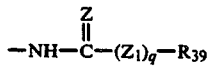

wherein Z is oxygen or sulfur, $Z_1$ is oxygen or —NH—, q is 0 or 1, and $R_{39}$ is hydrogen, alkyl of 1 to 6 carbons, mono- and dihaloalkyl of 1 to 6 carbons, phenyl or substituted phenyl having 1 or 2 halo, alkyl (of 1 to 6 carbons) or alkoxy (of 1 to 6 carbons) substituents, provided that (i) when z is oxygen, $Z_1$ is —NH— and q is 1, and (ii) when $Z_1$ is oxygen and q is 1, $R_{39}$ is other than hydrogen; or a radical of the formula

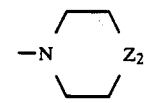

wherein $Z_2$ is a direct bond, —CH$_2$—, oxygen, or >N-$R_{40}$ wherein $R_{40}$ is hydrogen, alkyl of 1 to 6 carbons, hydroxyalkyl of 1 to 6 carbons, alkoxyalkyl (wherein each of the alkoxy and alkyl portions of the group has 1 to 6 carbons), alkanoyl of 1 to 6 carbons, alkylsulfonyl of 1 to 6 carbons, phenylmethylsulfonyl, alkoxycarbonyl of 2 to 7 carbons, alkoxycarbonylmethyl of 3 to 8 carbons, phenoxycarbonyl, aminocarbonyl, mono- and dialkylaminocarbonyl wherein the alkyl groups have 1 to 6 carbons, aminocarbonylmethyl, alkylaminocarbonylmethyl having 3 to 8 carbons, alkylaminothioxomethyl wherein the alkyl group has 1 to 6 carbons, (alkylthio)thioxomethyl wherein the alkyl group has 1 to 6 carbons, phenyl, phenylmethyl, benzoyl, or substituted benzoyl having 1 or 2 halogen, alkyl of 1 to 6 carbons or alkoxy of 1 to 6 carbons substituents; and $R_{38}$ is hydrogen or nitro, provided that when $R_{38}$ is nitro, $R_{37}$ is amino.

Preferred compounds within the scope of formula VII are those wherein $R_{38}$ is hydrogen and $R_{36}$ is mono- or dihalophenyl, most preferably 2,4-dichlorophenyl. Ketoconazole (cis-1-acetyl-4-[4-[[2-(2,4-dichlorophenyl)-2-(1H-imidazol-1-ylmethyl)-1,3-dioxolan-4-yl]methoxy]phenyl]piperazine) is the most preferred compound of formula VII.

An eighth preferred group of imidazoles which can be used in this are the imidazolylethoxy derivative of quinoline-3-methanols. As disclosed in U.S. Pat. application Ser. No. 954,728 filed Oct. 25, 1978 antifungal and antibacterial activity is exhibited by compounds having the formula

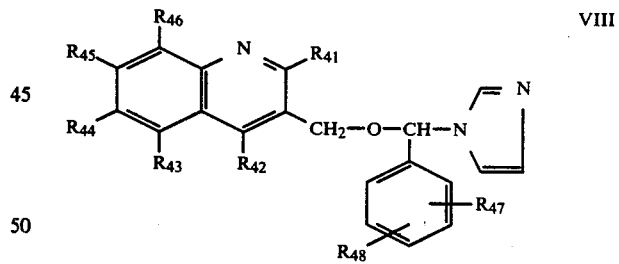   VIII or a physiologically acceptable acid-addition salt thereof, wherein $R_{41}$, $R_{42}$, $R_{43}$, $R_{44}$, $R_{45}$, $R_{46}$, $R_{47}$ and $R_{48}$ each is hydrogen, alkyl of 1 to 7 carbons, hydroxy, alkoxy of 1 to 7 carbons, alkylthio of 1 to 7 carbons or halogen. Preferred compounds of formula VIII are those wherein $R_{41}$, $R_{42}$, $R_{43}$, $R_{44}$, $R_{45}$, $R_{46}$, $R_{47}$ and $R_{48}$ each is hydrogen, alkyl of 1 to 4 carbons or halogen. The most preferred compounds of formula VIII are those wherein $R_{41}$, $R_{43}$ and $R_{46}$ each is hydrogen or halogen, especially hydrogen; $R_{42}$, $R_{44}$, $R_{45}$ and $R_{48}$ each is hydrogen or halogen, especially halogen and most especially chlorine; and $R_{47}$ and $R_{48}$ are attached in the 2- and 4-positions of the phenyl ring, respectively. Exemplary of the compounds of formula VIII are 4,6-dichloro-3-[[1-(2,4-dichlorophenyl)-2-(1H-imidazol-1-yl)ethoxy]-methyl]quinoline, monohydrochloride; 4,7- dichloro-3-[[1-(2,4-dichlorophenyl)-2-(1H-imidazol-1-yl)-ethoxy]methyl]quinoline, dihydrochloride; and 3-[[1-(2,4-dichlorophenyl)-2-(1H-imidazol-1-yl)-ethoxy]-methyl]quinoline.

The antifungal imidazole/antimicrobial agent compositions of this invention are useful for the treatment of vulvovaginitis and superficial dermatophytoses in mammals, particularly humans. They are particularly effective against *Candida albicans* and *Trichomonas vaginalis*. The weight ratio of imidazole to antimicrobial agent will be within the range of 1:10 to 10:1 and usually within the range of 1:5 to 5:1.

The compositions of this invention are intended for topical administration and can be formulated in any convenient pharmaceutical vehicle, over a wide range of concentrations, usually between about 0.1 to 10.0% by weight of the composition. Cream, ointment and lotion formulations are all known in the art and can each serve as the delivery system for the compositions of this invention. Other delivery systems are also known in the art and are useful for the compositions of this invention. For example, the compositions can be formulated as a tablet for intravaginal use or can be formulated as a liquid and impregnated on a tampon for intravaginal use. The above description of vehicles is exemplary only, and is not meant to limit the scope of this invention in any way.

Biological Testing

The following is a description of the agar or broth dilution "checkerboard" procedure used to demonstrate the synergistic properties of the compositions of this invention. cl Anticandidal Synergy Inoculum: Overnight cultures of the test yeasts (strains of *Candida albicans* and other Candida species) are prepared by inoculating a loopful of microorganisms from a slant into about 10 ml of F-4 broth. Inoculated broths are incubated at 37° C. for 18–20 hours which results in an organism density of about $10^8$ colony-forming units (CFU)/ml.

The inoculum level in the test is $10^4$ CFU. Just prior to use, the overnight broth cultures are diluted 1:10 in F-4 broth (producing $10^7$ CFU/ml.) The organisms are then placed into a template well and stamped onto prepared agar plates using the Denley Multipoint Inoculator A-400 (Denley Instruments, Sussex, England). The Denley Inoculator delivers 0.001 ml from each well thereby producing an inoculum of $10^4$ CFU for each organism.

Preparation of Plates: The antimicrobial agent and imidazole to be tested are dissolved in an appropriate diluent, e.g. water, buffer, dimethyl sulfoxide (DMSO), etc. If a diluent such as DMSO is employed sufficient dilutions are made so that the final concentration of DMSO in the plate is noninhibitory.

A scheme is presented for testing each drug at 25, 12.5, 6.3, 3.1, 1.6, 0.8, 0.4, 0.2 and 0.1 μg/ml and at all possible combinations of these levels in the mixture of antimicrobial agent and imidazole.

The antimicrobial agent and imidazole are prepared by dissolving 1 mg in 2 ml of water. Eight two-fold dilutions of each are prepared in F-4 broth. One ml of each concentration is then added to the appropriate test tube as outlined below.

|  |  | Highest concentration → | | | | | | | | | |
|---|---|---|---|---|---|---|---|---|---|---|---|
|  | A | A-1 | A-2 | A-3 | A-4 | A-5 | A-6 | A-7 | A-8 | A-9 | A-10 |
|  | B | B-1 | B-2 | B-3 | B-4 | B-5 | B-6 | . | . | . | . |
|  | C | C-1 | C-2 | C-3 | . | . | . | . | . | . | . |
|  | D | D-1 | . | . | . | . | . | . | . | . | . |
|  | E | . | . | . | . | . | . | . | . | . | . |
| Antimicrobial Agent | F | . | . | . | . | . | . | . | . | . | . |
|  | G | . | . | . | . | . | . | . | . | . | . |
|  | H | . | . | . | . | . | . | . | . | . | . |
|  | I | . | . | . | . | . | . | . | . | . | . |
|  | J | . | . | . | . | . | . | . | . | . | . |
|  |  | 1 | 2 | 3 | 4 | 5 | 6 | 7 | 8 | 9 | 10 |
|  |  |  |  | Imidazole |  |  |  |  |  |  | ↑ |
|  |  |  |  |  |  |  |  |  | Highest concentration of Imidazole | | |

To each tube in vertical row 1 and horizontal row J add 1.0 ml of F-4 broth (therefore J-1 receives 2.0 ml of F-4 broth and contains no drug). To horizontal row A (tubes A-1 through A-10) add 1.0 ml of the 0.5 mg/ml concentration of antimicrobial agent (the highest concentration). To horizontal row B, add 1.0 ml of the first serial dilution of antimicrobial agent (0.25 mg/ml). Repeat this procedure throughout the remaining horizontal rows using the next serial dilutions (concentrations used in decreasing order). Therefore row A has the highest concentration of antimicrobial agent row I has the lowest concentration. Row J does not receive antimicrobial agent. To vertical row 10 (tubes A-10 through J-10) add 1.0 ml of the 0.5 mg/ml concentration of imidazole (the highest concentration of imidazole). To vertical row 9, add 1.0 ml of the first serial dilution of imidazole (0.25 mg/ml). Repeat this procedure through the remaining vertical rows using the next serial dilutions (concentrations used in decreasing order). Row 1 does not receive imidazole. All test tubes should now have a total of 2.0 ml.

Label petri dishes A-1 through B-1 through B-10, . . ., and J-1 through J-10. Add 1.0 ml from the appropriate tube to the corresponding dish. To each dish then add 9.0 ml of F-4 agar cooled to about 50° C. Swirl the dishes to mix drugs and agar thoroughly. Let the dishes cool. Prepare a start, between and a stop dish each containing 10.0 ml of F-4 agar. These are growth control dishes.

Test Run: Each dish is inoculated with $10^4$ CFU of each test organism and incubated at 37° C. for 18–20 hours. Organisms are scored (+), (+) or (−). The scores (+) and (+) indicate growth while (−) indicates complete inhibition of growth.

Interpretation of Results: Rows 1 and J provide the respective minimum inhibitory concentrations of antimicrobial agent and imidazole alone. The minimum inhibitory concentration (MIC) is defined as the lowest concentration of a compound giving complete inhibition of growth (a(−) score).

The presence of synergistic interactions between the two test drugs can be determined by isobologram analysis. In constructing an isobologram for two drugs, the doses of the drugs are measured respectively on scales along two axes at right angles and experimental points representing the dose pairs producing a fixed biological response (in this case complete inhibition of growth of the test organism) are plotted. A curve fitted to the points is termed an isobole. The type of joint drug action occurring-synergism, addition or antagonism can be determined by the region of the isobolgram in which the isobole falls. When the two drugs are separately active (i.e. each when alone can produce the response concerned) the isobole extends from a point A on one axis of the isobologram, to a point B on the other (FIG. 1). Points A and B represent the respective MIC's of antimicrobial agent and imidazole. If the isobole is a straight line AB for two drugs, they are said to show additive action or addition. If, on the contrary, the isobole lies within the triangle OAB synergy is said to occur, and if outside the rectangle OACB antagonism occurs.

Antidermatophyte and Antitrichomonal Synergy

The above described broth dilution "checkerboard" procedure (*Trichophyton mentagrophytes* and *Trichomonas vaginalis* are substituted for *Candida albicans* and Candida species) is used to demonstrate the synergistic properties of the compositions of this invention.

The following three tables summarize the experimental work done using the above procedures to demonstrate the synergism of the compositions of this invention.

TABLE 1

Azalomycin F - Imidazole Synergy vs. *Candida albicans*

| Imidazole | # of Strains Tested | Geometric Mean MIC (μg/ml) vs. Strains Tested | | # of Strains Synergistically Inhibited | Geometric Mean MIC (μg/ml) for Each Compound in Combination vs. Strains Showing Synergy | |
|---|---|---|---|---|---|---|
| | | Azalomycin F | Imidazole | | Azalomycin F | Imidazole |
| Econazole | 10 | 6.2 | 3.8 | 10 | 1.3 | 0.4 |
| Miconazole | 10 | 6.2 | 4.7 | 10 | 0.7 | 0.5 |
| SQ 80,365[1] | 10 | 6.2 | 25.0 | 10 | 0.9 | 3.5 |
| SQ 80,976[2] | 9 | 6.2 | 6.2 | 9 | 1.0 | 0.5 |
| SQ 80,898[3] | 10 | 5.8 | 8.2 | 10 | 1.0 | 0.5 |
| SQ 81,037[4] | 10 | 9.4 | 12.5 | 10 | 1.0 | 1.3 |
| Clotrimazole | 6 | 3.9 | 2.5 | 6 | 0.3 | 0.3 |
| Tioconazole | 10 | 3.8 | 12.5 | 10 | 0.7 | 1.4 |
| Ketoconazole | 10 | 5.4 | 50.0 | 10 | 1.0 | 0.5 |
| SQ 80,558[5] | 10 | 6.2 | 10.1 | 10 | 1.0 | 1.3 |
| SQ 80,955[6] | 10 | 6.2 | 8.2 | 10 | 0.9 | 1.0 |
| SQ 80,896[7] | 10 | 9.4 | 6.2 | 10 | 1.5 | 1.1 |
| SQ 80,986[8] | 10 | 6.2 | 7.1 | 10 | 1.3 | 1.1 |

Footnotes from Table 1
[1] SQ 80,365 is 4-chloro-5-[[1-(2,4-dichlorophenyl)-2-(1H—imidazol-1-yl)ethoxy]methyl]-1-ethyl-3-methyl-1H—pyrazolo[3,4-b]pyridine, hydrochloride (1:1).
[2] SQ 80,976 is 4-chloro-5-[[1-(2,4-dichlorophenyl)-2-(1H—imidazol-1-yl)ethoxy]methyl]-1-methyl-1H—pyrazolo[3,4-b]pyridine, hydrochloride (1:1).
[3] SQ 80,898 is 2,4-dichloro-5-[[1-(2,4-dichlorophenyl)-2-(1H—imidazol-1-yl)ethoxy]methyl]pyridine, hydrochloride (1:1).
[4] SQ 81,037 is 4,6-dichloro-3-[[1-(2,4-dichlorophenyl)-2-(1H—imidazol-1-yl)ethoxy]methyl]-2-methylpyridine, hydrochloride (1:1).
[5] SQ 80,558 is 4,7-dichloro-3-[[1-(2,4-dichlorophenyl)-2-(1H—imidazol-1-yl)ethoxy]methyl]quinoline, hydrochloride (1:1).
[6] SQ 80,955 is 4,6-dichloro-3-[[1-(2,4-dichlorophenyl)-2-(1H—imidazol-1-yl)ethoxy]methyl]quinoline, hydrochloride (1:1).
[7] SQ 80,896 is 1-(3-chloro-10,11-dihydro-5H—dibenzo[a,d]cyclohepten-5-yl)-1H—imidazole, hydrochloride (1:1).
[8] SQ 80,986 is 1-(10,11-dihydro-3-methyl-5H—dibenzo[a,d]cyclohepten-5-yl)-1H—imidazole, hydrochloride.

TABLE 2

Azalomycin F - Econazole Synergy

| Organism | # of Strains Tested | Geometric Mean MIC (μg/ml) vs. Strains Tested | | # of Strains Synergistically Inhibited | Geometric Mean MIC (μg/ml) For Each Compound in Combination vs. Strains Showing Synergy | |
|---|---|---|---|---|---|---|
| | | Azalomycin F | Econazole | | Azalomycin F | Econazole |
| *Candida albicans* | 10 | 5.6 | 5.6 | 10 | 1.3 | 0.3 |
| *Candida tropicalis* | 3 | 6.2 | 12.5 | 3 | 1.3 | 2.1 |
| *Candida krusei* | 2 | 6.2 | 1.6 | 2 | 2.2 | 0.3 |
| *Candida parakrusei* | 2 | 4.4 | 2.2 | 2 | 2.0 | 0.6 |
| *Candida pseudotropicalis* | 1 | 3.1 | 3.1 | 1 | 0.9 | 0.9 |
| *Candida guilliermondii* | 1 | 3.1 | 0.4 | 1 | 1.6 | 0.2 |
| *Candida stellatoidea* | 1 | 6.2 | 12.5 | 1 | 1.2 | 2.4 |
| *Trichomonas vaginalis* | 1 | 7.8 | 15.6 | 1 | 3.0 | 4.4 |
| *Trichomonas foetus* | 1 | 15.6 | 31.2 | 1 | 5.9 | 9.8 |
| *Trichophyton mentagrophytes* | 1 | 1.6 | 0.003 | 1 | 0.8 | 0.0015 |

TABLE 3

Synergist - Econazole Synergy vs. *Candida albicans*

| Synergist | # of Strains Tested | Geometric Mean MIC (g/ml) vs. Strains Tested | | # of Strains Synergistically Inhibited | Geometric Mean MIC (μg/ml) for Each Compound in Combination vs. Strains Showing Synergy | |
|---|---|---|---|---|---|---|
| | | Synergist | Econazole | | Synergist | Econazole |
| Azalomycin F | 10 | 5.6 | 5.6 | 10 | 1.3 | 0.3 |
| Anisomycin | 10 | 34.2 | 5.6 | 10 | 5.7 | 0.4 |

TABLE 3-continued

Synergist - Econazole Synergy vs. *Candida albicans*

| Synergist | # of Strains Tested | Geometric Mean MIC (g/ml) vs. Strains Tested | | # of Strains Synergistically Inhibited | Geometric Mean MIC (µg/ml) for Each Compound in Combination vs. Strains Showing Synergy | |
|---|---|---|---|---|---|---|
| | | Synergist | Econazole | | Synergist | Econazole |
| Brefeldin A | 10 | 20.1 | 5.6 | 10 | 0.7 | 0.1 |
| EM4940 A | 10 | 100 | 4.7 | 10 | 16.5 | 0.2 |
| EM4940 A & B | 10 | 100 | 12.5 | 10 | 25.0 | 0.5 |
| EM 4940 B | 10 | 100 | 11.7 | 10 | 25.0 | 0.8 |

The following is a detailed description of the diffusion assay used to demonstrate the synergistic properties of a composition comprising ascomycin and econazole.

Qualitative Assessment

An agar diffusion assay is employed. Essentially imidazole is incorporated into a Candida seeded agar medium at a concentration well below its inhibitory concentration e.g. 1/5 or 1/10 its MIC. Various concentrations of antimicrobial agent are prepared and placed on filter paper discs and applied to dishes with and without imidazole. If the zone of inhibition produced by the antimicrobial agent in the presence of imidazole is greater than that seen in the absence of imidazole, synergy has occurred.

Procedure: An overnight culture of *Candida albicans* is prepared by inoculating a loopful of microorganisms from a slant into about 10 ml of F-4 broth. Inoculated broths are incubated at 37° C. for 18-20 hours which results in an organism density of about $10^8$ CFU/ml. Three flasks of F-4 agar are prepared. To one flask 1/5 the minimum inhibitory concentration of imidazole for the test Candida strain is added. To the second flask 1/10 the MIC of imidazole is added and to the third no drug is added. The three flasks then received a 1% inoculum of a 1:10 dilution of the overnight of *Candida albicans*. This results in a density of $10^5$ CFU/ml of the test organism in the plates. The seeded agar with and without imidazole is poured into petri dishes and allowed to solidify. The antimicrobial agent is solubilized and fixed concentrations are applied to filter paper discs (6.35 mm diameter). After drying sets of discs are applied onto the dishes. The dishes are then incubated at 37° C. for 18-20 hours at which time the zones of inhibition produced by imidazole are measured. Results are plotted as concentration of imidazole vs. diameter of the zone of inhibition.

The increase in the zones of inhibition seen with ascomycin in the presence of subinhibitory concentrations of econazole indicates that these two drugs interact synergistically vs. *Candida albicans*.

F-4 Medium

The compositons of the F-4 medium used in the above tests is as follows:

| | |
|---|---|
| Tryptone | 5 grams |
| Malt extract | 3 grams |
| Glucose | 10 grams |
| Yeast extract | 3 grams |
| Distilled water to | 1 liter |
| Sterilize 121° C. for | 15 minutes. |

If solid medium is desired, 15 grams of agar are added per liter.

What is claimed is:

1. A composition for the treatment of a fungal infection comprising a combination of azalomycin F and econazole, wherein the weight ratio of azalomycin F to econazole is from about 8:1 to 1:4.

* * * * *